US00PP14751P2

(12) United States Plant Patent

Ritchie et al.

(10) Patent No.: US PP14,751 P2
(45) Date of Patent: May 4, 2004

(54) COROKIA PLANT NAMED 'TUTTI FRUTTI'

(50) Latin Name: *Corokia cotoneaster×Corokia virgata*
Varietal Denomination: Tutti Frutti

(76) Inventors: John Stanley Ritchie, 4 Higginson Street, Otane (NZ); Kathleen Anne Ritchie, 4 Higginson Street, Otane (NZ)

( * ) Notice: Subject to any disclaimer, the term of this patent is extended or adjusted under 35 U.S.C. 154(b) by 0 days.

(21) Appl. No.: 10/624,106

(22) Filed: Jul. 21, 2003

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—C. A. Whealy

(57) ABSTRACT

A distinct cultivar of Corokia plant named "Tutti Frutti", characterized by its upright plant form; freely branching growth habit; and green, yellow and brownish red tri-colored foliage.

1 Drawing Sheet

Botanical classification/cultivar designation: *Corokia cotoneaster×Corokia virgata* cultivar Tutti Frutti.

BACKGROUND OF THE INVENTION

The present Invention relates to a new and distinct cultivar of Corokia plant, botanically known as *Corokia cotoneaster×Corokia virgata*, and hereinafter referred to by the name 'Tutti Frutti'.

The new Corokia was discovered by the Inventors in 1997 in a controlled environment in Otane, New Zealand, from seedling progeny from a chance cross-pollination of an unidentified *Corokia cotoneaster* selection, not patented, as the female, or seed, parent with an unidentified *Corokia virgata* selection, not patented, as the male, or pollen, parent.

Asexual reproduction of the new Corokia by cuttings in a controlled environment in Otane, New Zealand since 1999, has shown that the unique features of this new Corokia are stable and reproduced true to type in successive generations.

SUMMARY OF THE INVENTION

Plants of the cultivar Tutti Frutti have not been observed under all possible environmental conditions. The phenotype may vary somewhat with variations in environment such as temperature and light intensity without, however, any variance in genotype.

The following traits have been repeatedly observed and are determined to be the unique characteristics of 'Tutti Frutti'. These characteristics in combination distinguish 'Tutti Frutti' as a new and distinct cultivar:

1. Upright plant form.
2. Freely branching growth habit.
3. Green, yellow and brownish red tri-colored foliage.

Plants of the cultivar Tutti Frutti are most similar to plants of the parents, the unidentified selections of *Corokia cotoneaster* and *Corokia virgata*. In side-by-side comparisons conducted in Otane, New Zealand, plants of the new Corokia differed from plants of the parent selections primarily in leaf size and leaf coloration.

BRIEF DESCRIPTION OF THE PHOTOGRAPHS

The accompanying colored photographs illustrate the overall appearance of the new Corokia, showing the colors as true as it is reasonably possible to obtain in colored reproductions of this type. Colors in the photographs may differ slightly from the color values cited in the detailed botanical description which accurately describe the colors of the new Corokia.

The photograph at the top of the sheet comprises a side perspective view of a typical plant of 'Tutti Frutti' grown in a container.

The photograph at the bottom of the sheet is a close-up view of typical leaves of 'Tutti Frutti'.

DETAILED BOTANICAL DESCRIPTION

In the following description, color references are made to The Royal Horticultural Society Colour Chart, 2001 Edition, except where general terms of ordinary dictionary significance are used. Plants used for the photographs and the following description were about two years old and grown under outdoor field conditions which closely approximate commercial production conditions in Boskoop, The Netherlands.

Botanical classification: *Corokia cotoneaster×Corokia virgata* cultivar Tutti Frutti.

Parentage:

*Female, or seed, parent.*—Unidentified selection of *Corokia cotoneaster*, not patented.

*Male, or pollen, parent.*—Unidentified selection of *Corokia virgata*, not patented.

Propagation:

*Type.*—By internode or tip cuttings.

*Time to initiate roots.*—Summer: About 21 days at 32° C. Winter: About 30 days at 32° C.

*Time to produce a rooted cutting.*—About 42 days at 15° C.

*Root description.*—Fleshy; freely branching.

Plant description:

*Form.*—Perennial evergreen shrub; upright plant form; narrow inverted triangle; freely branching, dense and bushy habit; moderately vigorous.

*Plant height.*—About 43 cm.

*Plant diameter.*—About 20 cm.

*Lateral branches.*—Quantity per plant: About eight; pinching is not required. Length: About 18.9 cm. Diameter: About 3 mm. Internode length: About 1.6 mm. Strength: Strong. Texture: Densely pubescent. Color, young: 166A, covered with pubescence, between N155A and 156D. Color, mature: N200A.

*Foliage description.*—Arrangement: Alternate, simple. Length: About 3.7 cm. Width: About 1.1 cm. Shape: Oblanceolate. Apex: Acute. Base: Cuneate. Margin: Entire. Texture, upper and lower surfaces: Slightly leathery. Developing leaves with pubescence on upper and lower surfaces. Fully expanded leaves with pubescence towards the leaf base on the upper surface; lower surface, densely pubescent. Luster: Upper surface, glossy; lower surface, dull. Venation pattern: Pinnate. Color: Developing foliage, upper surface: N144A; towards the base and margin, 175B to 175C. Developing foliage, lower surface: Surface not visible, densely pubescent, 155C. Fully expanded foliage, upper surface: Random areas of green, N144A to 144B, and yellow, 7D; towards base and margin, 175B to 175C. Fully expanded foliage, lower surface: Surface not visible, densely pubescent, 155C. Venation, upper and lower surfaces: Same as lamina. Petioles: Length: About 2 mm. Diameter: About 1.2 mm. Texture: Densely pubescent. Color: 175B to 175C covered with pubescence, 155C.

Flower description: Flower development has not been observed.

Disease/pest resistance: Plants of the new Corokia have not been noted to be resistant to pathogens and pests common to Corokia.

Temperature tolerance: Plants of the new Corokia are hardy to USDA Zones 8 to 9 and have been observed to tolerate temperatures as high as 35° C.

It is claimed:

1. A new and distinct cultivar of Corokia plant named 'Tutti Frutti', as illustrated and described.

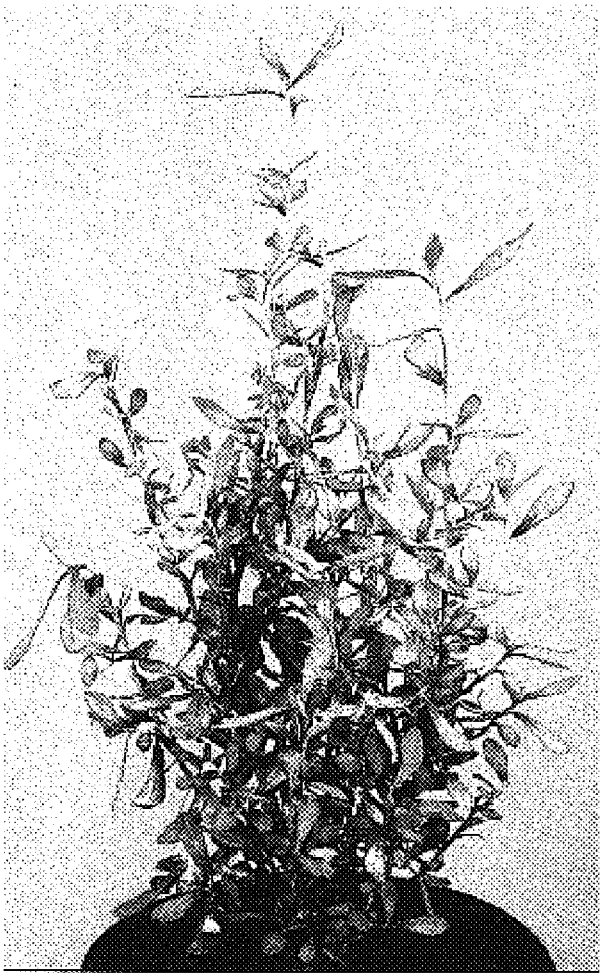
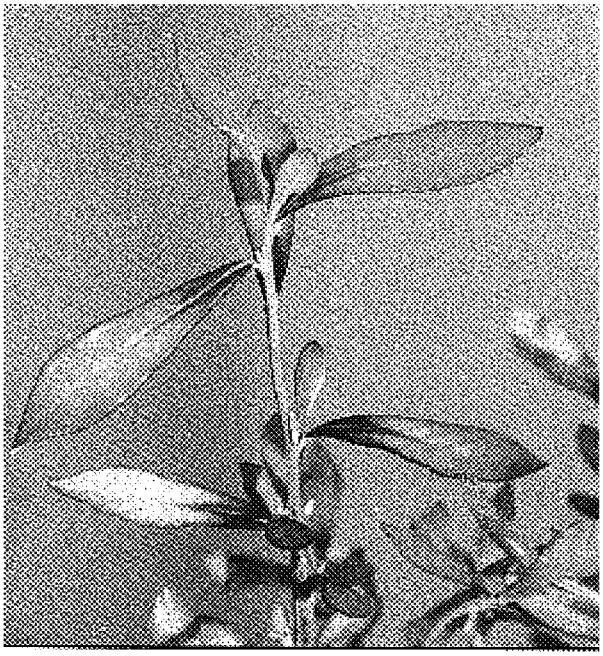

* * * * *